United States Patent [19]

Bohuon

[11] 4,080,472

[45] Mar. 21, 1978

[54] METFORMIN 2-(P-CHLOROPHENOXY)-2-METHYLPROPIONATE

[75] Inventor: Claude Bohuon, Paris, France

[73] Assignee: Societe d'Etudes et d'Exploitation de Marques et Brevets S.E.M.S., France

[21] Appl. No.: 751,964

[22] Filed: Dec. 17, 1976

Related U.S. Application Data

[63] Continuation of Ser. No. 558,920, Mar. 17, 1975, abandoned.

[30] Foreign Application Priority Data

Mar. 22, 1974  France .............................. 74 099630

[51] Int. Cl.$^2$ ................ A61K 31/205; A61K 31/155; C07C 129/00

[52] U.S. Cl. .............................. 424/316; 260/501.14; 424/326

[58] Field of Search .............................. 424/326, 316; 260/501.14

[56] References Cited

FOREIGN PATENT DOCUMENTS 1,900,772  10/1969  Germany .......................... 260/501.14
2,247,378  3/1974   Germany.

*Primary Examiner*—Sam Rosen

[57] ABSTRACT

A new salt, metformin clofibrate, is disclosed. This salt has useful therapeutic properties and can be used in the control of glycaemia and cholesterolaemia and in the treatment of atheromatous conditions.

3 Claims, No Drawings

METFORMIN 2-(P-CHLOROPHENOXY)-2-METHYLPROPIONATE

This is a continuation of application Ser. No. 558,920, filed Mar. 17, 1975, now abandoned.

The present invention relates to the metformin salt of clofibric acid. (Clofibric acid is also known as 2-p-chlorophenoxy-2-methyl-propionic acid, and metformin is the biguanide, 1,1-dimethylbiguanide.) It also relates to a process for the preparation of this salt and its application in therapy.

Metformin clofibrate according to this invention is metformin monoclofibrate and is represented by the formula:

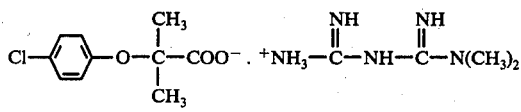

This salt can be prepared from metformin and clofibric acid by a method which is in itself known.

Since the free base of metformin is not commercially available, it is preferred, according to the process of this invention, to use metformin hydrochloride as starting material. According to this preferred process, metformin hydrochloride, dissolved in a lower alcohol, especially methanol containing 2% by volume of water, is contacted with an anionic resin in order to obtain metformin base. Metformin base is then contacted with clofibric acid in acetone to produce the salt of this invention.

A preparative Example which serves to illustrate the invention is given below. This Example illustrates the manufacture of approximately 5 kg of metformin monoclofibrate.

EXAMPLE

The equipment consists of:
tanks for preparing and storing the solutions,
a 40 liter column (useful height: 1.50 m),
a 150 liter reactor and
the customary filtration and drying equipment.
The starting materials consist of:

| | |
|---|---|
| metformin hydrochloride | 3,000 g(18.1 mols) |
| clofibric acid | 3,885 g(18.1 mols) |
| methanol | 242 l |
| acetone | 100 l |
| an aqueous solution of sodium hydroxide of concentration 40 g/l | 100 l |
| demineralised water | 500 l |
| anionic resin (Duolite A 101 D) | 25 kg. |

The resin is introduced into the column, using demineralised water, and regenerated (because commercially available Duolite A 101 D resin is in the chloride form) by passing the sodium hydroxide solution through and then rinsing with demineralised water until the eluate becomes neutral (approximately 400 liters of demineralised water have to be used). The column is then rinsed with 100 liters of methanol containing 2% by volume of water, this having proved to be the best exchange solvent.

The metformin hydrochloride is dissolved in 82 liters of methanol containing 2% by volume of water and the solution thus obtained is passed over the resin. The chloride content of the eluate collected is checked to ensure that it is $\leq$ 50 ppm relative to the solution.

The column is then rinsed with 60 liters of methanol containing 2% by volume of water and the resulting eluate is combined with the above eluate. The total eluate is 142 liters of a solution of metformin base.

The total eluate is concentrated to dryness in vacuo and at an external temperature of 40° C, which can rise to 60° C at the end of the concentration process so as to remove the water completely.

When all the solvent is removed, metformin base solidifies in the form of a light yellow solid (theoretical yield of the order of 99%). This dry metformin base can be converted immediately into a salt when contacted with clofibric acid; before the step of converting it to a salt, it can still contain 1% (by weight) of metformin hydrochloride without subsequent disadvantage. The methanol is recovered from the distillate.

The resin is rinsed with 100 liters of demineralised water and the entrained methanol is recovered by this rinsing process. At this stage, the column is ready for a further operation, beginning with the regeneration process.

The metformin base, in the concentration reactor is dissolved in 100 liters of acetone, with stirring. A small amount of coloured insoluble material (consisting mainly of unrecovered metformin hydrochloride) which may be present is filtered off and clofibric acid in the solid state is immediately added to the filtrate, with stirring.

The clofibric acid dissolves as the metformin clofibrate crystallises out (it can happen that this crystallisation takes place before the acid has completely dissolved; this does not have any subsequent effects). Stirring is continued for 4 hours after the start of crystallisation.

The solution containing the metformin clofibrate which has been formed is stored in a cold chamber.

The solution is then filtered to collect the metformin clofibrate formed, followed by rinsing using 4 times 5 liters of chilled acetone and maximum suction-drying. The acetone is recovered from the filtrate, and the metformin clofibrate is dried in a ventilated oven set at 40° C.

5 Kg, or a little more, of metformin clofibrate, in the form of a white crystalline powder, are thus obtained, corresponding to a total yield of approximately 80% relative to the theoretical amount calculated from the stoichiometric amounts of metformin hydrochloride and clofibric acid employed. If care is taken partially to concentrate the solution of metformin base in acetone (for example, by removing approximately 15 liters of acetone therefrom) in vacuo at ambient temperature, the yield can be increased to 90 - 95%.

The melting point of metformin clofibrate is 165° C (as measured in a capillary tube).

From the physical point of view, this salt, which can only be anhydrous initially, has a melting point that is different from that of clofibric acid (120° C as measured in a capillary tube) and from metformin base (110° C as measured in a capillary tube).

The infra-red spectrum is different from that of the spectra of clofibric acid, metformin base and the equimolecular mixture of clofibric acid and metformin base. The infra-red spectrum demonstrates that a salt has been formed because the peaks at 2,700, 2,500, 1,600 and 1,300 cm$^{-1}$ of the free COOH group of clofibric acid and the peak at 1,320 cm$^{-1}$ of metformin base do not appear in the case of the salt.

Taking account of the analytical results, there is considerable evidence that the salt obtained according to the invention is metformin monoclofibrate, that is to say the equimolecular salt.

Finally, metformin clofibrate is soluble in cold water (1 g in 5 ml of water) and gives solutions with a pH close to neutral. This salt is also very soluble in methanol and ethanol. It is sparingly soluble in acetone (1 g in 100 ml) at ambient temperature, and insoluble in benzene, chloroform and hexane.

The results of pharmacological experiments have shown that the salt of this invention possesses advantageous properties different from the sum of those of clofibric acid and metformin. In relation to the toxicity, the following values were obtained in mice of the Swiss strain:

$LD_{50}$ by oral administration: 1.60 g/kg $LD_{50}$ by intraperitoneal administration: 0.85 g/kg The salt of this invention possesses a hypoglycaemia-inducing action on alloxan-diabetic rabbits. In relation to the hypocholesterol-aemia-inducing action, an improvement in the lipid deposits has been observed in rabbits receiving a hypercholesterol-aemia-inducing diet and in genetically diabetic obese mice, this improvement being marked at the arterial level.

The salt of this invention thus makes it possible to control glycaemia without the danger of hypoglycaemia occurring, and to treat and prevent vascular complications in diabetes. It also makes it possible to treat and prevent atheromatous conditions.

Therapeutic compositions containing metformin clofibrate and a non-toxic carrier or diluent are provided by the invention. These compositions will preferably be administered orally or parenterally, the daily dose depending on whether the patient is, or is not, diabetic.

If the patient is diabetic, the daily dose is decided in relation to the glycaemia. On the other hand, if the patient is not diabetic, the daily dose of metformin clofibrate will be 0.5 to 2 g, divided up into several doses.

I claim:

1. A compound which is metformin monoclofibrate.
2. A therapeutic composition consisting essentially of an effective amount of metformin monoclofibrate and a non-toxic carrier or diluent.
3. A method of controlling glycaemia and/or alleviating atheromatous conditions in a mammal, said method consisting essentially of administering to said mammal an effective amount of metformin monoclofibrate.

* * * * *